United States Patent [19]

Konstantinov et al.

[11] 4,168,547
[45] Sep. 25, 1979

[54] ANTERIOR-CHAMBER LENS-CARRIER

[75] Inventors: Nikola I. Konstantinov; Dimiter V. Benchev, both of Sofia, Bulgaria

[73] Assignee: Medicinska Akademia, Sofia, Bulgaria

[21] Appl. No.: 783,826

[22] Filed: Apr. 1, 1977

[51] Int. Cl.$^2$ .............................................. A61F 1/24
[52] U.S. Cl. ................................................................ 3/13
[58] Field of Search ............................................ 3/13, 1

[56] References Cited

U.S. PATENT DOCUMENTS

| 3,673,616 | 7/1972 | Fedorov et al. | 3/13 |
| 3,922,728 | 12/1975 | Krasnov | 3/13 |
| 3,925,825 | 12/1975 | Richards et al. | 3/13 |
| 3,986,214 | 10/1976 | Krasnov | 3/13 |
| 4,073,014 | 2/1978 | Poler | 3/13 |

FOREIGN PATENT DOCUMENTS 1103399  5/1955  France ............................................ 3/13

OTHER PUBLICATIONS

"Artiphakia and Aniseikonia" by R. C. Troutman, American Journal of Ophthalmology, vol. 56, No. 2, Oct. 1963, pp. 630–632.

*Primary Examiner*—Ronald L. Frinks
*Attorney, Agent, or Firm*—Karl F. Ross

[57] ABSTRACT

An anterior-chamber lens assembly in which a unitary lens carrier is stamped from thin sheet material and includes a ring formed with a throughgoing lens opening and a pair of diametrically opposed long flat arms extending outwardly from the ring and adapted to bend around the edge of the opening of the iris and extend therebehind, and three angularly equispaced flat short arms extending outwardly from the ring to a distance less than the long arms. A lens having a groove formed in the outer periphery thereof is positioned in the lens opening with the inner periphery of the opening received in the groove and completely filling it.

2 Claims, 5 Drawing Figures

ANTERIOR-CHAMBER LENS-CARRIER

FIELD OF THE INVENTION

This invention is related in general, to lens carriers and, more particularly, an anterior chamber lens carrier made by punching-out hostophane, which is generally well-accepted by the human eye.

BACKGROUND OF THE INVENTION

All varieties of known anterior chamber lenses feature carriers with either nylon-thread loops or lugs. The medallion-shaped Binkhorst-lens is characterized by two nylon-loops disposed in a horizontal plane and twin-perforated plates to be sutured in the eye, to the iris.

The making and the mounting of such carriers from nylon-thread and lugs is a slow and labor-consuming process. Each lens is separately perforated for the manual passing through of the nylon thread or for the fastening of lugs.

A skillfull technician can prepare only 4 to 5 lenses per day. In sum, all these factors make the lens-production expensive and seriously impede its mass application.

OBJECTS OF THE INVENTION

It is therefore an object of the present invention to provide a carrier for anterior chamber lenses which obviate the drawbacks mentioned above.

SUMMARY OF THE INVENTION

A groove is formed around the circumference of the lens, and a hostaphane ring which is a registered trademark for foils and combinated foils, manufactured by Kalle, a branch of the Firm Hoechst AG, Wiesbaden, Biebrich, Germany and is composed of polyterephthalate, polyethylene (high and low density), polyvinylidene chloride and copolymers thereof, and aluminum, is mounted in the groove of the lens and is formed with arms protruding therefrom to fasten the carrier to the iris of the pupil. Obtained is a well-tolerated implant for the eye, which can be inexpensively mass produced.

The carrier is represented in three separate embodiments of the invention depending upon the disposition of the arms projecting from the hostaphane ring. The first embodiment comprises five arms and is intended for snap fastening of the lens in position in the iris. The second embodiment is four-armed ring and is designed to be fastened to the iris by means of two horizontal and opposite arms which are introduced into preliminary formed slots in the iris. Finally, the third embodiment is a simplification of the second. It has in fact, only two arms and can be fixed in a horizontal plane and of the iris as described for the second embodiment or turned by 90 degrees, whereas the bottom arm is fixed in a slot formed in the iris and the upper arm is sutured to it.

The advantages of the lens-carrier of all three embodiments lies in the fact that it is light-weight and is well tolerated by the eye, having been tested on humans and rabbits, and is easily manufactured by means of sheet stamping and finally, it is easy to mount in the groove of the lens.

BRIEF DESCRIPTION OF THE DRAWING

The above and other objects, features and advantages of the invention will become more readily apparent from the following description, reference being made to the accompanying drawing in which.

SPECIFIC DESCRIPTION

Figures 1, 2:
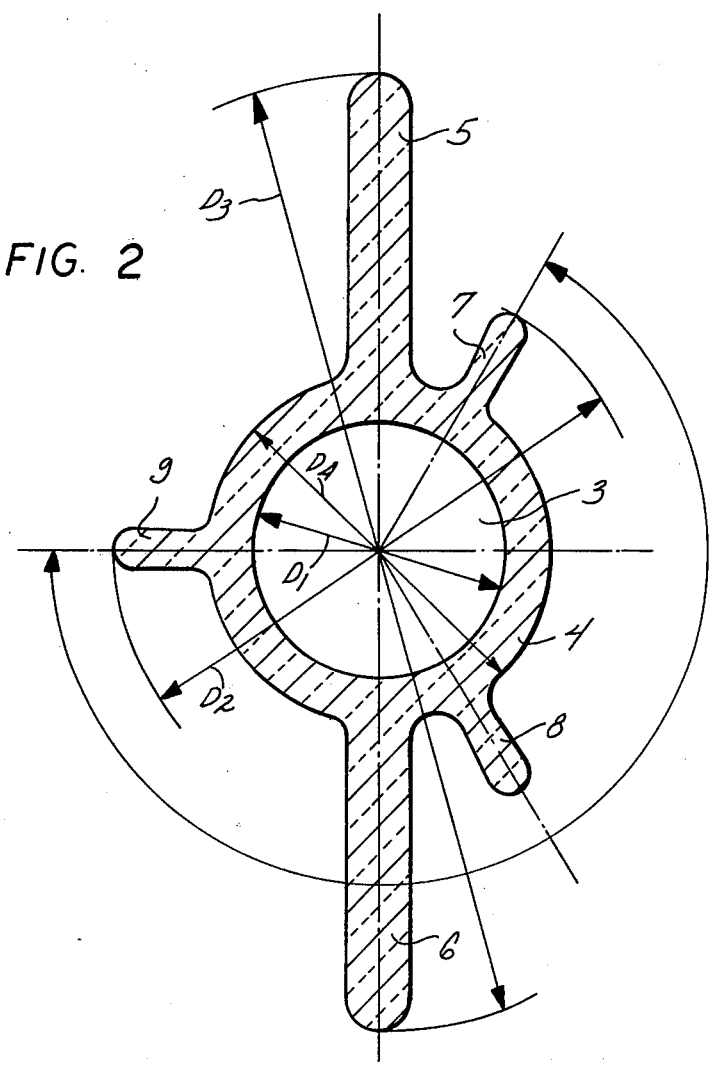
FIG. 1 is axial section of the anterior chamber lens.
FIG. 2 is a carrier for the anterior chamber lens, comprising five arms.
Figure 3:
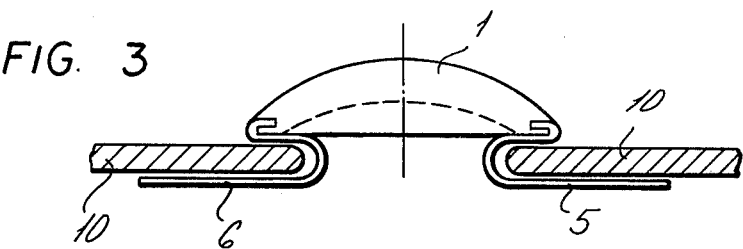
FIG. 3 is a mounting diagram of the carrier of FIG. 2.
Figure 4:
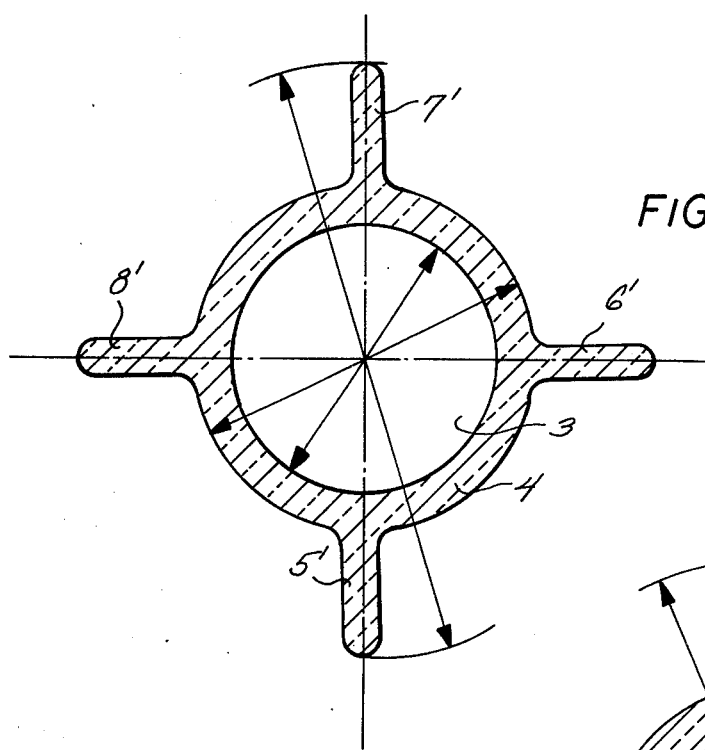
FIG. 4 is a four-armed lens-carrier.

The unitary carrier comprises a ring 4, forming a lens opening 3 having a diameter $D_1$. The ring 4 has an outer diameter $D_4$ approximately 1.33 times greater than diameter $D_1$, according to the first embodiment of the invention includes two diametrically opposed long arms 5 and 6 extending to a diameter $D_3$, approximately 3.66 times greater than diameter $D_1$, as well as three shorter arms 7, 8 and 9 extending to a diameter $D_2$, approximately 2.13 times greater than the diameter $D_1$ and disposed at intervals of 120° and lying in a common plane with arm 9 being disposed at 90° to arms 5 and 6. In accordance with another embodiment of the invention, the ring 4 comprises four arms 5', 6', 7' and 8', which are uniform and of equal length, being disposed at 90° intervals on the ring and lying in a common plane therewith. Finally, the third embodiment features a ring 4 having two opposed arms 5" and 6" lying—in a common plane.

Figure 5:
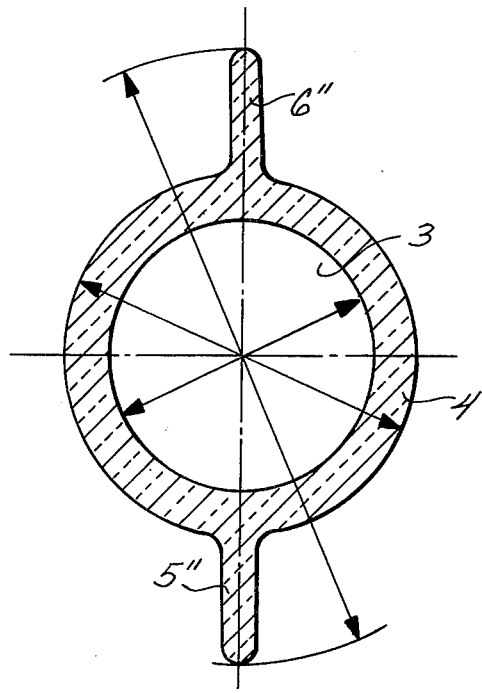
FIG. 5 is a twin-armed anterior-chamber lens carrier.

In use, the ring 4 is attached to the lens 1 by being fitted into the circumferential groove 2. According to the first embodiment the long arms 5 and 6 are bent behind the iris 10 and are used to fasten the lens to the pupil, while the short arms 7, 8 and 9 remain in front of the iris. In the second embodiment, the horizontal arms 6' and 8' are introduced into preliminary-made slots in the iris, whereas the rays 5' and 7' remain in front of the iris, thus assuring a free movement of the iris. The third embodiment teaches a horizontal orientation of both arms 5" and 6" and their insertion into slit-shaped apertures formed in the iris, or, as shown in FIG. 5, a vertical orientation of the arms, with the bottom arm 5 being inserted into the slit formed in the iris and the upper arm sutured to it.

What we claim is:

1. An anterior-chamber lens assembly comprising:
 a unitary lens carrier stamped from thin sheet material composed of polyterephthalate, polyethylene (high and low density), polyvinylidene chloride and copolymers thereof, and aluminum, said lens carrier including:
 a ring,
 a throughgoing lens opening formed in said ring and having a continuous inner periphery,
 a pair of diametrically opposed long, flat, solid arms formed on said ring from said sheet material and extending outwardly therefrom and coplanar therewith, said long arms being adapted to bend around the edge of the opening of the iris and therebehind, and
 three angularly equispaced flat, solid short arms formed on said ring form said sheet material and extending outwardly therefrom and coplanar therewith, to a distance less than said long arms, said short arms being adapted to overlie the front of the iris, the long arms being wider than the short arms; and a lens having a continuous groove formed in the outer periphery thereof and adapted to be positioned in said lens opening with said inner periphery received in said groove and completely filling same, one of said short arms being perpendicular to said long arms.

2. The carrier defined in claim 1 wherein said short arms extending to an imaginary circle having a diameter equal to approximately 2.13 times the diameter of said lens opening and said long arms extending to an imaginary circle having a diameter equal to approximately 3.66 times the diameter of said lens opening.

* * * * *